United States Patent [19]

Kwan

[11] Patent Number: 4,847,079

[45] Date of Patent: Jul. 11, 1989

[54] BIOLOGICALLY STABLE INTERFERON COMPOSITIONS COMPRISING THIMEROSAL

[75] Inventor: Henry K. H. Kwan, Summit, N.J.

[73] Assignee: Schering Corporation, Kenilworth, N.J.

[21] Appl. No.: 77,957

[22] Filed: Jul. 27, 1987

Related U.S. Application Data

[63] Continuation of Ser. No. 759,817, Jul. 29, 1985, abandoned.

[51] Int. Cl.⁴ ............................................. A61K 45/02
[52] U.S. Cl. .................................. 424/85.7; 424/85.4
[58] Field of Search ................... 424/85.4, 85.5, 85.6, 424/85.7

[56] References Cited

U.S. PATENT DOCUMENTS 4,230,696  10/1980  Hashem ................................. 514/17
4,478,822  10/1984  Haslam et al. ........................ 424/85
4,496,537  1/1985  Kuan ..................................... 424/85

FOREIGN PATENT DOCUMENTS 82481  6/1983  European Pat. Off.
176216  10/1984  Japan.
181223  10/1984  Japan.

OTHER PUBLICATIONS

Derwent Abstract 84-285308/46 of Japanese Application 176,216/84.
English Translation of the Abstract of the Above-Identified Japanese Application.

Primary Examiner—Blondel Hazel
Attorney, Agent, or Firm—Anita W. Magatti; Stephen I. Miller

[57] ABSTRACT

Stable pharmaceutical compositions comprising interferon and thimerosal which are substantially resistant to microorganism contamination and growth are disclosed.

12 Claims, No Drawings

BIOLOGICALLY STABLE INTERFERON COMPOSITIONS COMPRISING THIMEROSAL

This is a continuation of application Ser. No. 759,817 filed July 29, 1985 now abandoned.

SUMMARY OF THE INVENTION

The present invention relates to pharmaceutical compositions comprising interferon which are substantially resistant to microorganism contamination and growth during storage at room temperature.

In particular, the preservative thimerosal (i.e. sodium ethylmercurithiosalicylate, also known as merthiolate) is present in the compositions as an antimicrobial preservative.

Formulations of the present invention are useful in preparing stable interferon solutions suitable for injectable, ophthalmic and nasal products.

BACKGROUND OF THE INVENTION

Interferons have great potential as drugs for the treatment of a variety disease states, e.g. various types of viral infections and certain cancers.

As used herein, the term "interferon" includes natural and recombinant alpha (leucocyte) and beta (fibroblast) interferons, but alpha interferons are preferred. As used herein, the term "alpha interferon" means a natural or recombinant interferon exhibiting biological properties similar to those of human leucocyte interferon. It should be noted that a number of alpha interferon species are known, usually designated by a numeral after the Greek letter, and all are contemplated for use in this invention. Also included within the scope of this invention are the so-called alpha hybrid interferons wherein fragments of two or more native alpha interferon species are joined (see for instance, EP No. 51873). Preferred forms of alpha interferon for use in the formulations of the present invention are alpha-1 and alpha-2 interferon. Particularly preferred for use in the formulations of the present invention is alpha-2 interferon. Alpha-2 interferon may be prepared by recombinant-DNA methods, for example those disclosed by Nagata et al., *Nature,* Vol. 284, pages 316–320 (1980), and by Weissmann, European Patent No. 32,134.

Biologically stable interferon compositions are known. See Kwan U.S. Pat. No. 4,496,537, herein incorporated by reference, which claims a method of improving biological stability of an interferon formulation comprising the addition of glycine or alanine to an alpha interferon formulation prior to lyophilization. While such lyophilized powders are not generally susceptible to microbiological contamination since interferon formulations are commonly prepared under aseptic conditions, reconstituted solutions of these lyophilized formulations are susceptible to microbiological contamination and growth. This makes reconstituted solutions unsuitable for multiple dose applications, e.g. nasal or ophthalmic applications, where the solution will not be used all at once.

Various preservatives and preservative combinations have been tested, but in general have been found to cause physical instability such as precipitation or turbidity in the reconstituted solution. Some preservatives are also ineffective in preventing microbial contamination and/or reduce interferon activity.

DETAILED DESCRIPTION

I have surprisingly found that of the many preservatives tested, only thimerosal is effective in preventing microbial contamination in a reconstituted interferon solution for at least four weeks when the reconstituted solution is stored at room temperature or under refrigeration. Furthermore, such reconstituted solutions are stable with respect to antiviral activity, pH and physical appearance under those conditions. Thimerosal can be incorporated with the interferon in the lyophilized powder or can be added in the diluent for reconstitution of lyophilized interferon powder. The concentration of thimerosal in the solution may be in the range of 0.005 to 1 mg/ml, with 0.02 to 0.05 mg/ml being preferred, and 0.02 mg/ml being most preferred.

A particular advantage of the present invention is the ability to store the reconstituted solution at room temperature safely and effectively for prolonged periods. This advantage is evident especially for opthalmic and nasal preparation where a non-hospitalized patient will be self-administering the formulations for an extended time period, e.g. 1–3 weeks, and a portable and easily stored formulation is desirable. Another advantage is the increased comfort of the patient in being able to use such formulations as eye drops or nasal sprays at room temperature.

The various preservatives and preservative combinations compared to thimerosal were tested by reconstituting lyophilized alpha interferon formulations with a vehicle comprising the preservative or preservative combination. Reconstituted solutions stored at room temperature and under refrigeration were evaluated periodically for one month for physical stability and appearance; interferon activity was determined initially, after 7 days, 14 days and at the end of the study by the standard method of the inhibition of cytopathic effect (CPE) of virus. Samples which were stable for at least 7 days at room temperature were further tested using the USP XX Antimicrobial Preservative Effectiveness (APE) Test and the British Pharmacopeia (BP) test for antimicrobial preservative effectiveness.

The following Table 1 gives the results of the testing of physical stability of the interferon formulations to which various preservatives and preservative combinations were added:

TABLE 1

| Preservative | Concentration % | Compatibility with alpha-Interferon* |
|---|---|---|
| Benzalkonium Chloride | 0.005 | P |
|  | 0.02 | P |
| Benzyl Alcohol | 0.9 | CR |
|  | 1.8 | P |
| Chlorhexidine Gluconate | 0.005 | P |
|  | 0.01 | P |
| Chlorobutanol | 0.5 | CR |
| Methylparaben/ Propylparaben | 0.12/0.012 | CR |
| Phenylmercuric Acetate | 0.004 | CR |
| Phenylethyl Alcohol | 0.5 | P |
| Phenol | 0.25 | P |
| Benzyl Alcohol + Methylparaben + Propylparaben | 0.9 0.08 0.01 | CR |
| Benzyl Alcohol + Chlorobutanol | 0.9 0.3 | CR |
| Chlorhexidine Gluconate + Methylparaben + Propylparaben | 0.005 0.08 0.01 | CR |
| Phenylethyl Alcohol + | 0.5 | CR |

TABLE 1-continued

| Preservative | Concentration % | Compatibility with alpha-Interferon* |
|---|---|---|
| Methylparaben + Propylparaben | 0.08 0.01 | |
| Chlorhexidine Gluconate + Chlorobutanol | 0.005 0.5 | P |
| Chlorobutanol + Methylparaben + Propylparaben | 0.5 0.08 0.01 | P |
| Thimerosal | 0.002 | C |
| | 0.005 | C |

*C — compatible for at least 7 days at refrigeration (REF) and room temperature (RT)
CR — compatible for at least 7 days at REF, but not at RT
P — turbidity and/or precipitation occurs within 7 days at REF and RT Alpha interferon solutions prepared from thimerosal-containing lyophilized powders and from thimerosal-containing diluents passed physical stability, APE and CPE tests. Alpha interferon solutions prepared from thimerosal-containing diluents also passed the BP test for antimicrobial preservative effectiveness.

Alpha inteferon compositions tested comprised $1 \times 10^7$, $2.5 \times 10^7$ and $5 \times 10^7$ International units (I.U.) interferon/ml, although it is contemplated that compositions of the present invention may contain a range of $2 \times 10^3$ to $5 \times 10^8$ I.U./ml, preferably $1 \times 10^4$ to $2 \times 10^8$ I.U. alpha interferon/ml. The specific activity of the alpha interferon used in the compositions of the present invention should be at least $5 \times 10^7$ I.U./mg total protein, preferably at least $1 \times 10^8$ I.U./mg total protein. In addition to alpha inteferon and thimerosal, the pharmaceutical solutions of the present invention contain 0-2 mg albumin/ml and 5-25 mg glycine/ml in a compatible buffer to maintain the pH at 6.5 to 8.0. Preferably the compositions comprise 1 mg albumin/ml and 20 mg glycine/ml in a sodium dibasic phosphate and sodium monobasic phosphate buffer system at a pH of 7.0 to 7.4.

When thimerosal is added to the alpha interferon solution before lyophilization, the diluent for reconstitution may be purified water. When thimerosal is added to alpha interferon lyophilized powder, the diluent may be water, but is preferably an aqueous solution of a compatible buffer to maintain the pH at a level which will prevent decomposition of thimerosal. The buffer system may be the same as that used in the alpha interferon lyophilized powder, e.g. pH 6.5 to 7.5 sodium phosphate buffer, but preferably is a pH 3.5 to 5.5 citric acid buffer prepared from citric acid (monohydrate or anydrous) and sodium citrate (dihydrate or anhydrous).

Following are examples of alpha-2 interferon formulations wherein thimerosal is present in the diluent and wherein thimerosal is present in the lyophilized powder.

EXAMPLE 1

| | mg/ml |
|---|---|
| Lyophilized Powder* | |
| Alpha-2 Interferon | $2 \times 10^3$-$2 \times 10^8$ I.U. |
| Sodium Phosphate Dibasic | 1-5 |
| Sodium Phosphate Monobasic | 0.2-1.0 |
| Aminoacetic Acid | 5-25 |
| Human Albumin | 0.5-2 |
| Preserved Diluent for Reconstitution (A) | |
| Thimerosal | 0.005-0.1 |
| Sodium Phosphate Dibasic | 0.2-1.0 |
| Sodium Phosphate Monobasic | 0.4-2.0 |
| Purified Water q.s. ad | 1.0 ml |
| Preserved Diluent for Reconstitution (B) | |
| Thimerosal | 0.005-0.1 |
| Sodium Citrate Dihydrate | 0.1-0.5 |
| Citric Acid Monohydrate | 0.1-0.5 |
| Purified Water q.s. ad | 1.0 ml |

EXAMPLE 2

| Lyophilized Powder* | mg/ml |
|---|---|
| Alpha-2 Interferon | $2 \times 10^3$-$2 \times 10^8$ I.U. |
| Sodium Phosphate Dibasic | 1-5 |
| Sodium Phosphate Monobasic | 0.2-1.0 |
| Aminoacetic Acid | 5-25 |
| Human Albumin | 0.5-2 |
| Thimerosal | 0.005-0.1 |

*Lyophilized powder may contain other stabilizers to improve/enhance Interferon stability.

Lyophilized powders are prepared by combining and lyophilizing the ingredients for the powder formulations using standard techniques.

Diluents are prepared by combining the ingredients of the diluents using standard techniques.

I claim:

1. A biologically and physically stable pharmaceutical solution substantially resistant to microorganism contamination and growth comprising $2 \times 10^3$ to $5 \times 10^8$ I.U. alpha interferon, 0-2 mg human albumin, 5-25 mg glycine, 0.005 to 1.0 mg thimerosal, and a compatible buffer system to maintain the pH at 6.5 to 8.0 per milliliter of solution.

2. A pharmaceutical solution of claim 1 comprising $1 \times 10^4$ to $2 \times 10^8$ I.U. alpha interferon/ml.

3. A pharmaceutical solution of claim 2 wherein the pH is maintained at 7.0 to 7.4.

4. A pharmaceutical solution of claim 3 comprising 1 mg human albumin/ml and 20 mg glycine/ml.

5. A pharmaceutical solution of claim 4 comprising 0.02 to 0.05 mg thimerosal/ml.

6. A pharmaceutical solution of claim 5 wherein the alpha interferon is alpha-2 interferon.

7. A biologically stable lyophilized pharmaceutical composition substantially resistant to microorganism contamination and growth, for reconstitution with water, comprising $2 \times 10^3$ to $5 \times 10^8$ I.U. alpha interferon, 0-2 mg human albumin, 5-25 mg glycine, 0.005 to 1.0 mg thimerosal and a compatible buffer system to maintain the pH of the reconstituted solution at 6.5 to 8.0 for each milliliter of water that will be added later during reconstitution.

8. A pharmaceutical composition of claim 7 comprising $1 \times 10^4$ to $2 \times 10^8$ I.U. alpha interferon per milliliter of water to be added later during reconstitution.

9. A pharmaceutical composition of claim 8 wherein the buffer is chosen so that the pH of the reconstituted solution is maintained at pH 7.0 to 7.4.

10. A pharmaceutical composition of claim 9 wherein 1 mg human albumin and 20 mg glycine are added per milliliter of water to be added later during reconstitution.

11. A pharmaceutical composition of claim 10 wherein 0.02 to 0.05 mg thimerosal is added per milliliter of water to be added later during reconstitution.

12. A pharmaceutical composition of claim 11 wherein the alpha interferon is alpha-2 interferon.

* * * * *